United States Patent
Popovic et al.

(10) Patent No.: US 11,083,529 B2
(45) Date of Patent: Aug. 10, 2021

(54) CONTINUOUS IMAGE INTEGRATION FOR ROBOTIC SURGERY

(71) Applicant: KONINKLIJKE PHILIPS N.V., Eindhoven (NL)

(72) Inventors: Aleksandra Popovic, Bostom, MA (US); Aryeh Leib Reinstein, Bronx, NY (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 1023 days.

(21) Appl. No.: 15/112,709

(22) PCT Filed: Jan. 14, 2015

(86) PCT No.: PCT/IB2015/050271
§ 371 (c)(1),
(2) Date: Jul. 20, 2016

(87) PCT Pub. No.: WO2015/110934
PCT Pub. Date: Jul. 30, 2015

(65) Prior Publication Data
US 2016/0331475 A1    Nov. 17, 2016

Related U.S. Application Data

(60) Provisional application No. 61/931,168, filed on Jan. 24, 2014.

(51) Int. Cl.
*A61B 1/00* (2006.01)
*A61B 34/30* (2016.01)
(Continued)

(52) U.S. Cl.
CPC ............ *A61B 34/30* (2016.02); *A61B 1/0016* (2013.01); *A61B 34/20* (2016.02); *A61B 90/361* (2016.02);
(Continued)

(58) Field of Classification Search
CPC .................................................. A61B 1/00149
(Continued)

(56) References Cited

U.S. PATENT DOCUMENTS

2012/0289777 A1* 11/2012 Chopra .............. A61B 1/00009
600/109
2014/0343571 A1   11/2014 Popovic
2014/0347353 A1   11/2014 Popovic

FOREIGN PATENT DOCUMENTS

| WO | 2011083374 A1 | 7/2011 |
| WO | 2012035492 A1 | 3/2012 |
| WO | 2013061225 A1 | 5/2013 |

OTHER PUBLICATIONS

Popovic, Aleksandra et al "An Approach to Robotic Guidance of an Uncalibrated Endoscope in Beating HEart Surgery", Proceedings of the 2010 3RD IEEE RAS & EMBS.

* cited by examiner

*Primary Examiner* — Alexandra L Newton

(57) ABSTRACT

A robot guiding system employing an endoscope (12), a robot (11), a robot controller (21), an endoscope controller (22) and an image integration module (24). In operation, the robot controller (21) command the robot (11) to move the endoscope (12) within the anatomical region, and the endoscope controller (22) generates an endoscopic video display (15) of an intra-operative endoscopic image of the anatomical region generated by the endoscope (12). As the endoscope (12) is stationary within the anatomical region, the image integration module (24) registers a pre-operative three-dimensional image of the anatomical region to the intra-operative endoscopic image of the anatomical region. As the endoscope (12) is moving within the anatomical region subsequent to the image registration, the image integration module (24) calibrates a motion of the robot (11)

(Continued)

relative to the endoscope (12) followed by tracking a motion of the endoscope (12) within the anatomical region.

9 Claims, 3 Drawing Sheets

(51) Int. Cl.
*A61B 34/20* (2016.01)
*A61B 90/00* (2016.01)
*A61B 17/00* (2006.01)

(52) U.S. Cl.
CPC ............... *A61B 2017/00725* (2013.01); *A61B 2034/2065* (2016.02); *A61B 2034/301* (2016.02); *A61B 2090/365* (2016.02)

(58) Field of Classification Search
USPC .................................................. 600/114–118
See application file for complete search history.

CONTINUOUS IMAGE INTEGRATION FOR ROBOTIC SURGERY

CROSS-REFERENCE TO PRIOR APPLICATIONS

This application is the U.S. National Phase application under 35 U.S.C. § 371 of International Application No. PCT/IB2015/050271, filed on Jan. 14, 2015, which claims the benefit of U.S. Provisional Patent Application No. 61/931,168, filed on Jan. 24, 2014. These applications are hereby incorporated by reference herein.

The present invention generally relates to robotic control of an endoscope during a minimally invasive surgical procedure (e.g., a minimally invasive coronary bypass grafting surgery). The present invention specifically relates to a continuous integration of pre-operative three-dimensional ("3D") images and intra-operative endoscopic images during a robotic assisted minimally invasive surgical procedure.

Two (2) imaging modalities are utilized during minimally invasive coronary bypass surgery. The first imaging modality is preoperative 3D imaging (e.g., computed-tomography ("CT"), magnetic resonance imaging ("MRI"), etc.) to extract information about geometry of coronary arteries. The second imaging modality is intraoperative endoscope imaging for real time visualization of the coronary arteries.

Generally, for robotic assisted minimally invasive coronary bypass surgery, a motion of the robot is known from encoders on the motors or other sensors that can report relative motion of the robot (e.g., absolute encoders mounted on robot axes or potentiometers), and a calibration of endoscope to robot is needed to compute correspondent endoscope motion. A camera calibration is further needed to know the amount of motion that needs to be applied to rendering camera so that the overlay is correctly visualized in the endoscope video. The two (2) calibrations are both time-consuming and prone to errors. They require specialized hardware and precise measurements and need to be performed by a trained professional. This can lead to extended operating room time, increased procedure cost, and limit clinical adaptation of the system.

To address the shortcomings of these two (2) calibrations, these image modalities may be integrated in multiple stages as known in the art. For example, a first stage may be an image registration stage that establishes a geometric relation between a 3D arterial tree from the preoperative 3D imaging and an arterial tree partially visible in the intraoperative endoscopic images. This image registration stage is primarily applicable to endoscopic coronary bypass surgery where bypass is performed under visual feedback from an endoscope and discloses various methods of guiding an endoscope with a robot using the merged information. Based on the geometric relation between the images, a second stage may be a preoperative overlay stage that overlays the 3D pre-operative volumetric arterial tree onto the 2D endoscopic images using an uncalibrated endoscope. This allows the surgeon to have important information from pre-operative scans available during surgery and registered to the anatomical region displayed in the endoscope. To enhance the preoperative overly, a third stage may be a motion compensation stage that facilitates an overlaying of deforming volumetric structures from pre-operative 3D images onto the 3D endoscopic images in order to compensate for any physiological motion of the anatomical structures which are displayed in an endoscope video.

This invention overcomes issues of updating registration information between pre-operative 3D images and live intra-operative endoscopic video in cases where the endoscope is moving as a result of motion of the robot holding the endoscope. This insures that the registration may be performed once at the beginning of the procedure after which the system continues to update the registration.

More particularly, the present invention continuously merges endoscope video and preoperative 3D images and display projection of the 3D images onto the 2D endoscope video during robotically assisted minimally invasive surgery. The present invention leverages the use of the aforementioned self-calibrating routines for both endoscope and robot so that no explicit calibration step is needed during the procedure. This will reduce operating time and improve robustness of the system as human error is eliminated.

One form of the present invention a robot guiding system employing an endoscope, a robot, a robot controller, an endoscope controller and an image integration module. In operation, the robot controller command the robot to move the endoscope within the anatomical region, and the endoscope controller generates an endoscopic video display of an intra-operative endoscopic image of the anatomical region generated by the endoscope. As the endoscope is stationary within the anatomical region, the image integration module registers a pre-operative three-dimensional image of the anatomical region to the intra-operative endoscopic image of the anatomical region. As the endoscope is moving within the anatomical region subsequent to the image registration, the image integration module calibrates a motion of the robot relative to the endoscope followed by tracking a motion of the endoscope within the anatomical region.

A second form of the present invention is a robot guiding method involving a generation of an intra-operative endoscopic image of an anatomical region by a stationary endoscope and a stationary registration of a pre-operative three-dimensional image of the anatomical region to the intra-operative endoscopic image of the anatomical region. The method subsequently involves generation of an intra-operative endoscopic image of an anatomical region by a moving endoscope and a motion registration of the pre-operative three-dimensional image of the anatomical region to the intra-operative endoscopic image of the anatomical region.

The term "pre-operative" as used herein is broadly defined to describe any activity executed before, during or after an endoscopic imaging of an anatomical region for purposes of acquiring a three-dimensional image of the anatomical region, and the term "intra-operative" as used herein is broadly defined to describe any activity executed by the robot unit and the control unit during an endoscopic imaging of the anatomical region. Examples of an endoscopic imaging of an anatomical region include, but are not limited to, a CABG, a bronchoscopy, a colonoscopy, a laparoscopy, and a brain endoscopy.

The foregoing forms and other forms of the present invention as well as various features and advantages of the present invention will become further apparent from the following detailed description of various embodiments of the present invention read in conjunction with the accompanying drawings. The detailed description and drawings are merely illustrative of the present invention rather than limiting, the scope of the present invention being defined by the appended claims and equivalents thereof.

Figure 1:
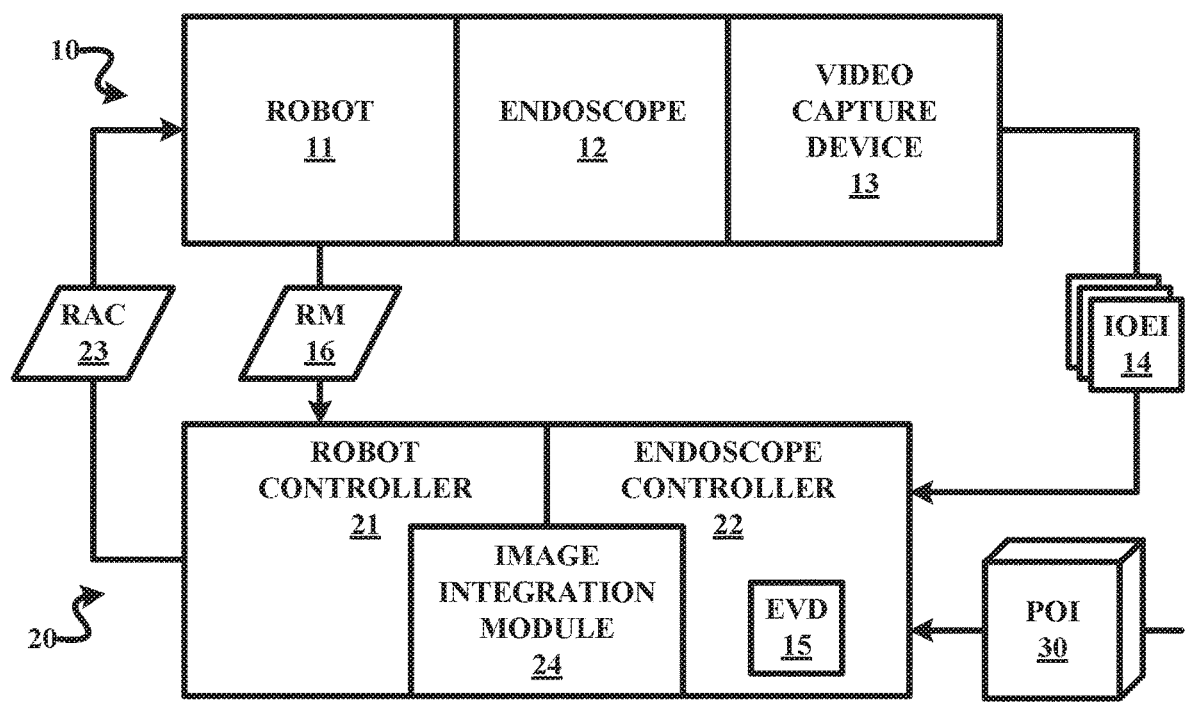
FIG. 1 illustrates an exemplary embodiment of a robotic guiding system in accordance with the present invention.

As shown in FIG. 1, a robotic guiding system employs a robot unit 10 and a control unit 20 for any endoscopic procedure, particularly endoscopic procedures involving an endoscopic imaging of a blood vessel tree having one or more furcations (i.e., branches). Examples of such endoscopic procedures include, but are not limited to, minimally invasive cardiac surgery (e.g., coronary artery bypass grafting or mitral valve replacement).

Robot unit 10 includes a robot 11, an endoscope 12 rigidly attached to robot 11 and a video capture device 13 attached to the endoscope 12.

Robot 11 is broadly defined herein as any robotic device structurally configured with motorized control of one or more joints for maneuvering an end-effector as desired for the particular endoscopic procedure. In practice, robot 11 may have four (4) degrees-of-freedom, such as, for example, a serial robot having joints serially connected with rigid segments, a parallel robot having joints and rigid segments mounted in parallel order (e.g., a Stewart platform known in the art) or any hybrid combination of serial and parallel kinematics.

Endoscope 12 is broadly defined herein as any device structurally configured with ability to image from inside a body. Examples of endoscope 12 for purposes of the present invention include, but are not limited to, any type of scope, flexible or rigid (e.g., endoscope, arthroscope, bronchoscope, choledochoscope, colonoscope, cystoscope, duodenoscope, gastroscope, hysteroscope, laparoscope, laryngoscope, neuroscope, otoscope, push enteroscope, rhinolaryngoscope, sigmoidoscope, sinuscope, thorascope, etc.) and any device similar to a scope that is equipped with an image system (e.g., a nested cannula with imaging). The imaging is local, and surface images may be obtained optically with fiber optics, lenses, and miniaturized (e.g. CCD based) imaging systems.

In practice, endoscope 12 is mounted to the end-effector of robot 11. A pose of the end-effector of robot 11 is a position and an orientation of the end-effector within a coordinate system of robot 11 actuators. With endoscope 12 mounted to the end-effector of robot 11, any given pose of the field-of-view of endoscope 12 within an anatomical region corresponds to a distinct pose of the end-effector of robot 11 within the robotic coordinate system. Consequently, each individual endoscopic image of a blood vessel tree generated by endoscope 12 may be linked to a corresponding pose of endoscope 12 within the anatomical region.

Video capture device 13 is broadly defined herein as any device structurally configured with a capability to convert an intra-operative endoscopic video signal from endoscope 12 into a computer readable temporal sequence of intra-operative endoscopic image ("IOEI") 14. In practice, video capture device 13 may employ a frame grabber of any type for capturing individual digital still frames from the intra-operative endoscopic video signal.

Still referring to FIG. 1, control unit 20 includes a robot controller 21 and an endoscope controller 22.

Robot controller 21 is broadly defined herein as any controller structurally configured to provide one or more robot actuator commands ("RAC") 26 to robot 11 for controlling a pose of the end-effector of robot 11 as desired for the endoscopic procedure. More particularly, robot controller 21 converts endoscope position commands ("EPC") 25 from endoscope controller 22 into robot actuator commands 26. For example, endoscope position commands 25 may indicate an endoscopic path leading to desired 3D position of a field-of-view of endoscope 12 within an anatomical region whereby robot controller 21 converts command 25 into commands 26 including an actuation current for each motor of robot 11 as needed to move endoscope 12 to the desired 3D position.

Endoscope controller 22 is broadly defined herein as any controller structurally configured to generate a endoscopic video display 15 of intra-operative endoscopic images ("IOEI") 14.

Figure 2:
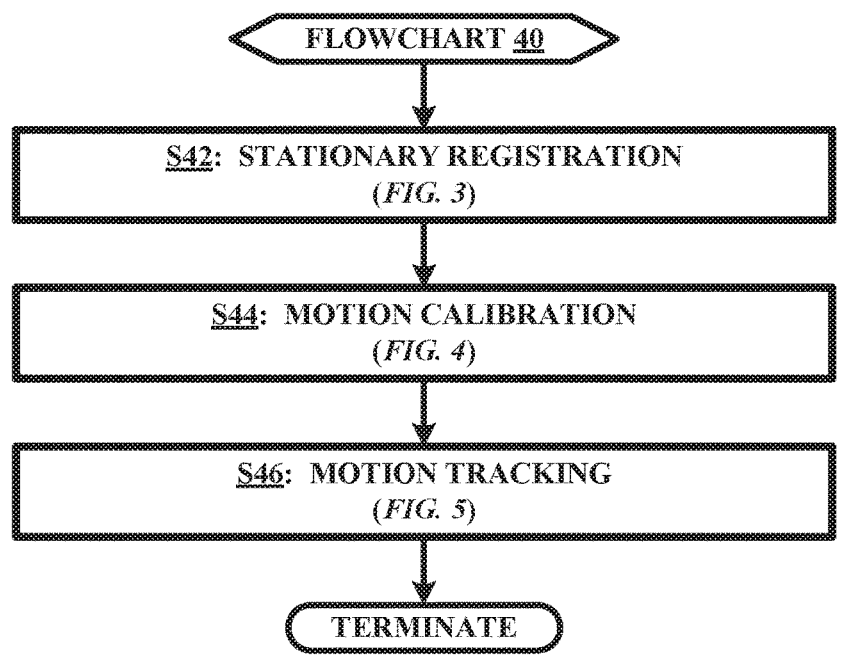
FIG. 2 illustrates a flowchart representative of an exemplary embodiment of a robotic guidance method in accordance with the present invention.

The present invention provides an image integration module 24 distributed between controllers 21 and 22 to execute a flowchart 40 as shown in FIG. 2 for a continuous integration of intra-operative endoscopic image 14 to a pre-operative 3D image ("POI") 30. A description of flowchart 40 will now be provided herein to facilitate a further understanding of image integration module 24. In practice, flowchart 40 may involve pre-steps of robot 11 being positioned whereby a center of rotation of robot 11 coincides with an entry point to a patient, and endoscope 12 being inserted in the patient's body to facilitate live video stream 15.

Referring to FIG. 2, a stage S42 of flowchart 40 encompasses a stationary registration of pre-operative 3D image 30 to intra-operative endoscopic image 40, a stage S44 of flowchart 40 encompasses a motion calibration of robot 11 to endoscope 12 derived from the stationary registration of stage S42, and a stage S46 of flowchart 40 encompasses a motion tracking of robot derived the motion calibration of stage S44.

Figure 3:
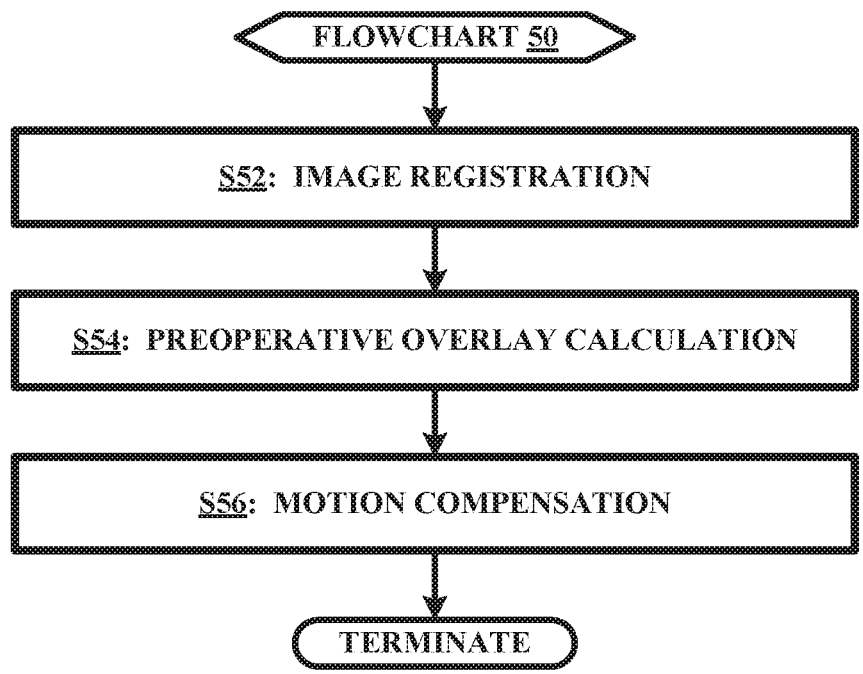
FIG. 3 illustrates a flowchart representative of an exemplary embodiment of a stationary registration method in accordance with the present invention.

A flowchart 50 as shown in FIG. 3 represents one embodiment of stage S42. A stage S52 of flowchart 50 encompasses module 24 registers pre-operative 3D image 30 to intra-operative endoscopic image 14 based on an arterial tree and/or venial tree as known in the art. In view of endoscope 12 not being calibrated, stage S52 will return a position of a virtual camera in the coordinate frame of 3D image 30 as a 4×4 transformation matrix $^{CT}T_{cam}$.

A stage S54 of flowchart 50 encompasses module 24 overlaying an extracted/segmented 3D volumetric arterial tree and/or venial tree onto intra-operative endoscopic image 14 as known in the art. The overlay will show projection of preoperative 3D image 30 onto endoscopic video display 15.

A stage S56 of flowchart 50 encompasses module 24 executing a motion compensation algorithm as known in the art for tracking a points on intra-operative endoscopic image 14 (e.g., nodes of arterial tree and/or venial tree) and updating the overlay image. More particularly, an execution of the motion compensation algorithm by module 24 compute a 3×3 matrix H that transforms a point from one endoscope view to another endoscope view:

$$\begin{bmatrix} x2 \\ y2 \\ 1 \end{bmatrix} = H \begin{bmatrix} x1 \\ y1 \\ 1 \end{bmatrix}.$$

Figure 4:
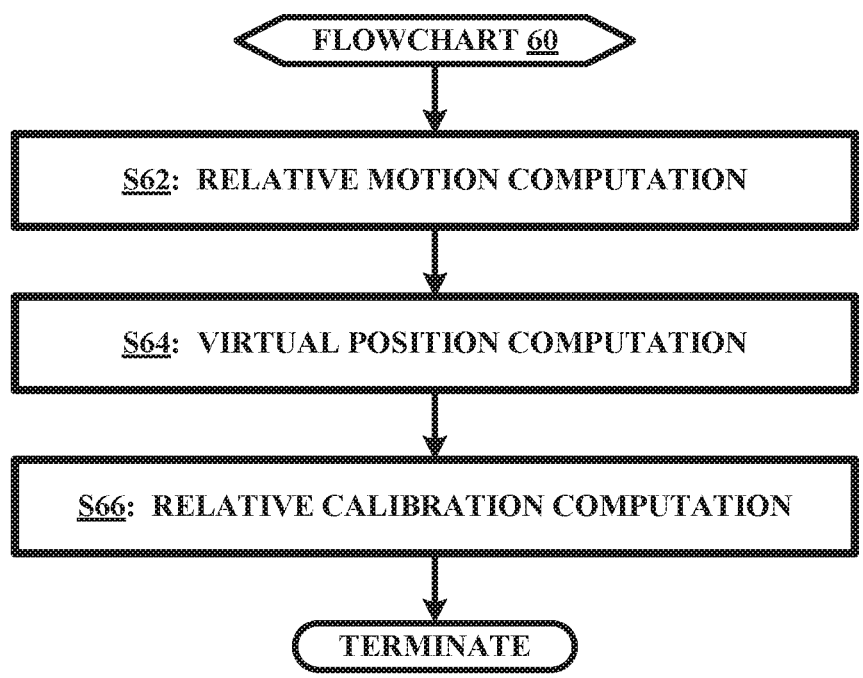
FIG. 4 illustrates a flowchart representative of an exemplary embodiment of a motion registration method in accordance with the present invention.

In one embodiment of stage S44 (FIG. 2), a flowchart 60 as shown in FIG. 4 involves a slow mode of robot operation to allow accurate tracking of points of endoscope view 14 (e.g., nodes of arterial tree and/or venial tree).

After the user performs the first motion of robot 11, a stage S62 of flowchart 60 encompasses module 24 recomputing the 2D endoscope points of stage S52 (FIG. 3) using homography matrix H of stage S56 (FIG. 3) and repeating stage S52 to calculate a camera transformation matrix after motion. Thereafter, using the transformation matrix before motion $$^{CT}_{before}T_{cam}^{-1}$$

and transformation matrix after motion $$^{CT}_{after}T_{cam},$$

total relative motion $^{CT}T_{cam}$ is computed:

$$^{CT}T_{cm} = ^{CT}_{before}T_{cam}^{-1} * ^{CT}_{after}T_{cam}.$$

A stage S64 of flowchart 60 encompasses module 24 recording robot tip position before motion $$^{robot}_{before}T_{tip}^{-1}$$

and after the motion $$^{robot}_{after}T_{tip}$$

derived from the use of robot encoders or other sensors as known in the art. Because of the uncalibrated nature of the system, exact tip position of is not known, thus the virtual tip position is used:

$$^{CT}T_{rm} = ^{robot}_{before}T_{tip}^{-1} * ^{robot}_{after}T_{tip}.$$

The virtual tip position can be any number larger than zero or a mathematical symbol.

For stage S66 of flowchart 60, relative calibration of robot to camera is computed as follows. In an ideal case, if the system is calibrated, $^{CT}T_{cm} = ^{CT}T_{rm}$ and the new registration can be computed by applying known robot motion to camera position. As the system is not calibrated and both camera position and robot tip position are not reflecting physical arrangement in the environment (e.g., an operating room), these two are related with a calibration matrix:

$$T_{calib}^{-1} {}^{CT}T_{cm} = ^{CT}T_{rm} * T_{calib}.$$

It is safe to assume that this matrix is constant during the entire length of the procedure. This assumption holds as long as the same endoscope 12 is used (same focal length of the camera). In cases where a different endoscope is introduced, the video stream is temporarily interrupted and image registration flowchart 50 will have to be executed for the new endoscope.

To continue stage S66, $$T_{calib}^{-1} {}^{CT}T_{cm} = ^{CT}T_{rm} * T_{calib}$$

is deduced from the rigid transformation for one position:

$$^{CT}T_{cam} = ^{robot}T_{tip} * T_{calib}.$$

Since both $^{CT}T_{cm}$ and $^{CT}T_{rm}$ are known, the $T_{calib}$ can be computed from $$T_{calib}^{-1} {}^{CT}T_{cm} = ^{CT}T_{rm} * T_{calib}.$$

This type of equation is called Sylvester equation and can be explicitly computed by one skilled in the art.

After stages S62-S66 are performed in the background, robot 11 is returned to a normal speed of operation as the tracking of the points is no longer necessary.

Figure 5:
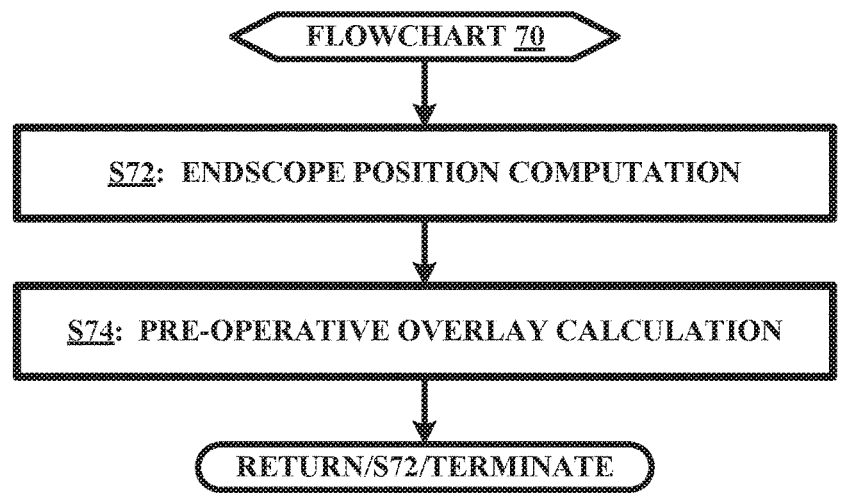
FIG. 5 illustrates a flowchart representative of an exemplary embodiment of a motion tracking method in accordance with the present invention.

In one embodiment of stage S46 (FIG. 2), a flowchart 70 as shown in FIG. 5 involves user performs another motion of robot 11 without the need for tracking points in intraoperative endoscopic image 14. As such, a stage S72 of flowchart 70 encompasses module 24 computing a new position $$^{CT}_{second\ motion}T_{camera}$$

of the camera of endoscope 13 from a new position of the robot $$^{robot}_{second\ motion}T_{tip} \text{ as } ^{CT}_{second\ motion}T_{camera} = ^{robot}_{second\ motion}T_{tip} * T_{calib}.$$

A stage S74 of flowchart 70 encompasses module 24 calculating a new overlay as taught by stage S54 (FIG. 3). Stages S72 and S74 are repeated until the end of the procedure or until a new registration for a new endoscope is required.

Referring back to FIGS. 2 and 4, an accuracy of stage S42 may be improved by repeating flowchart 60 for multiple times (N). For such repeats, stage S66 is modified to perform calculation of $T_{calib}$ from a system of N Sylvester-type equations. As this mathematical problem is overdefined, the solution can be find using optimization methods as known in art (e.g., Levenberg-Marquardt damped least square fitting). This can be repeated for N times or until the fitting error of the optimization algorithm returns error smaller than predefined accuracy requirement. This embodiment assures accurate image overlay by balancing duration of robot slow motion of flowchart 60.

Figure 6:
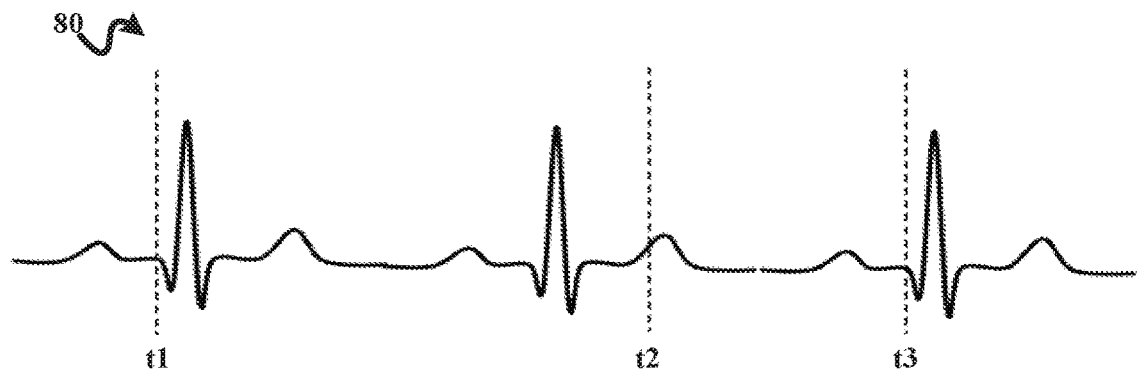
FIG. 6 illustrates an exemplary gated acquisition in accordance with the present invention.

Referring to FIGS. 2-4, stages S42 and S44 may be modified to address periodically moving organs (e.g., a heart). In this case, to separate heart motion from the motion of robot 11, stage S56 (FIG. 3) and stages S62 (FIG. 4) have to be performed at exactly same phase of the periodic motion. In this embodiment, an ECG signal can be used to gate acquisition of the endoscope images 14. For example, FIG. 6 shows a ECG signal 80. If the robot motion starts at time t1 and stops at time t2, module 24 will acquire the endoscope image 14 for homography matching stages S56 and S62 only after the heart returns to the same phase as in time t1 (e.g., time t3). This can be achieved by signal matching algorithms known in art.

Figure 7:
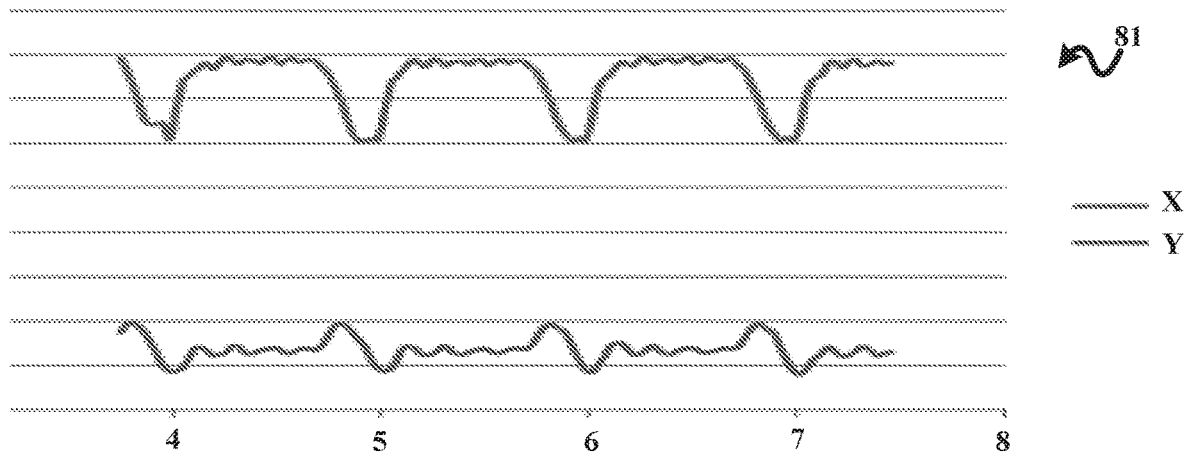
FIG. 7 illustrates an exemplary position trace in endoscope video in accordance with the present invention.

Alternatively, if an ECG signal is not available, module 24 may observe point motions on the heart as known in the art as exemplary shown with a position trace 81 shown in FIG. 7. The shape of these signals X and Y can be fitted to a forward signal filter and used to predict heart motion using forward filtering methods as known in art.

From the description of FIGS. 1-7 herein, those having ordinary skill in the art will appreciate the numerous benefits of the present invention including, but not limited to, an application of the present invention to any type of endoscopy surgery performed on any anatomical region.

While various embodiments of the present invention have been illustrated and described, it will be understood by those skilled in the art that the embodiments of the present invention as described herein are illustrative, and various changes and modifications may be made and equivalents may be substituted for elements thereof without departing from the true scope of the present invention. In addition, many modifications may be made to adapt the teachings of the present invention without departing from its central scope. Therefore, it is intended that the present invention not be limited to the particular embodiments disclosed as the best mode contemplated for carrying out the present invention, but that the present invention includes all embodiments falling within the scope of the appended claims.

The invention claimed is:

1. A robot guiding system, comprising:
   a robot unit including
     an endoscope operable to generate an intra-operative endoscopic image of an anatomical region, and
     a robot operably connected to the endoscope to move the endoscope within the anatomical region; and
   a control unit including
     a robot controller operably connected to the robot and configured to command the robot to move the endoscope within the anatomical region,
     an endoscope controller operably connected to the endoscope and configured to generate an endoscopic video display of the intra-operative endoscopic image of the anatomical region, and
     an image integration module operably distributed between the robot controller and the endoscope controller,
     wherein, as the endoscope is stationary within the anatomical region, the image integration module is configured to register a pre-operative three-dimensional image of the anatomical region to the intra-operative endoscopic image of the anatomical region, and
     wherein, as the endoscope is moving within the anatomical region subsequent to a registration of the pre-operative three-dimensional image and the intra-operative endoscopic image, the image integration module is further configured to calibrate a motion of the robot relative to the endoscope, and a motion calibration of the robot relative to the endoscope is in phase with a periodic motion of the anatomical region.

2. The robot guiding system of claim 1, wherein, subsequent to a motion calibration of the robot relative to the endoscope, the image integration module is further configured to track a motion of the endoscope.

3. The robot guiding system of claim 2, wherein a motion calibration of the robot relative to the endoscope is repeated multiple times by the image integration module prior to a tracking of the motion of the endoscope by the image integration module.

4. The robot guiding system of claim 1, wherein a registration of the pre-operative three-dimensional image and the intra-operative endoscopic image is in phase with a periodic motion of the anatomical region.

5. The robot guiding system of claim 1, wherein the image integration module is further configured to overlay a segmented portion of pre-operative three-dimensional image onto the intra-operative endoscopic image.

6. The robot guiding system of claim 5, wherein the image integration module is configured to update the overlay as a function of tracking at least one point on the intra-operative endoscopic image.

7. The robot guiding system of claim 1, wherein the image integration module is configured to compute a relative motion transformation matrix between the pre-operative three-dimensional image and the intra-operative endoscopic image as a function of a registration of the pre-operative three-dimensional image and the intra-operative endoscopic image and a function of tracking of features on the intra-operative endoscopic image as the endoscope is moved from a stationary position within the anatomical region.

8. The robot guiding system of claim 7, wherein the image integration module is configured to compute a position transformation matrix of a virtual position of the endoscope from a previous stationary position to a current position within the anatomical region.

9. The robot guiding system of claim 8, wherein the image integration module is configured to compute a relative calibration of the robot to the endoscope.

* * * * *